United States Patent [19]

Mussinan et al.

[11] 4,151,181
[45] Apr. 24, 1979

[54] MALTYL-2-METHYL ALKENOATES AND NOVEL PERFUME COMPOSITIONS AND PERFUMED ARTICLES CONTAINING SAME

[75] Inventors: Cynthia J. Mussinan, Bricktown; Braja D. Mookherjee; Frederick L. Schmitt, both of Holmdel, all of N.J.; Edward J. Shuster, Brooklyn, N.Y.

[73] Assignee: International Flavors & Fragrances Inc., New York, N.Y.

[21] Appl. No.: 884,381

[22] Filed: Mar. 8, 1978

[51] Int. Cl.² ...................... C07D 309/22; C11B 9/00
[52] U.S. Cl. ............................. 260/345.8 R; 252/522
[58] Field of Search ................................. 260/345.8 R

[56] References Cited

U.S. PATENT DOCUMENTS 3,907,718  9/1975  Hall et al. ........................... 560/205

*Primary Examiner*—Nicky Chan
*Attorney, Agent, or Firm*—Arthur L. Liberman; Franklin D. Wolffe

[57] ABSTRACT

Described are maltyl-2-methyl alkenoates having the structure:

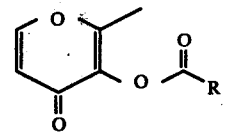

wherein R is an alkenyl moiety having one of the structures:

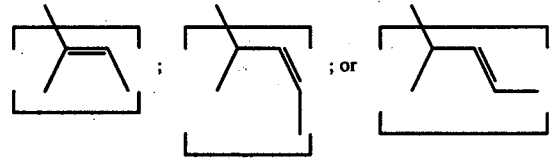

as well as the uses thereof in perfumery, that is, perfume compositions and perfumed articles as well as colognes of said compounds.

1 Claim, 8 Drawing Figures

GLC PROFILE FOR EXAMPLE I

GLC PROFILE FOR EXAMPLE II

IR SPECTRUM FOR EXAMPLE II

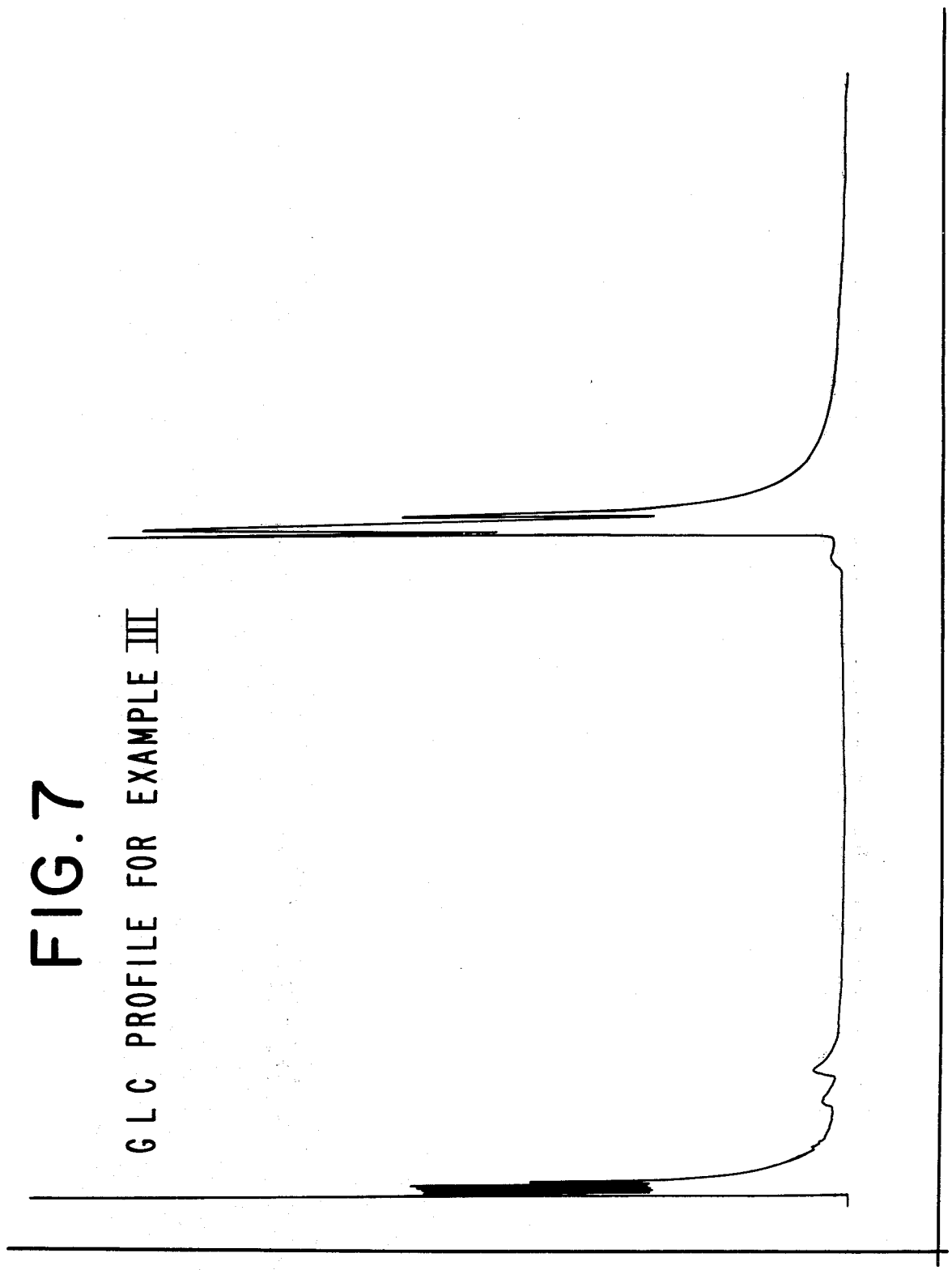

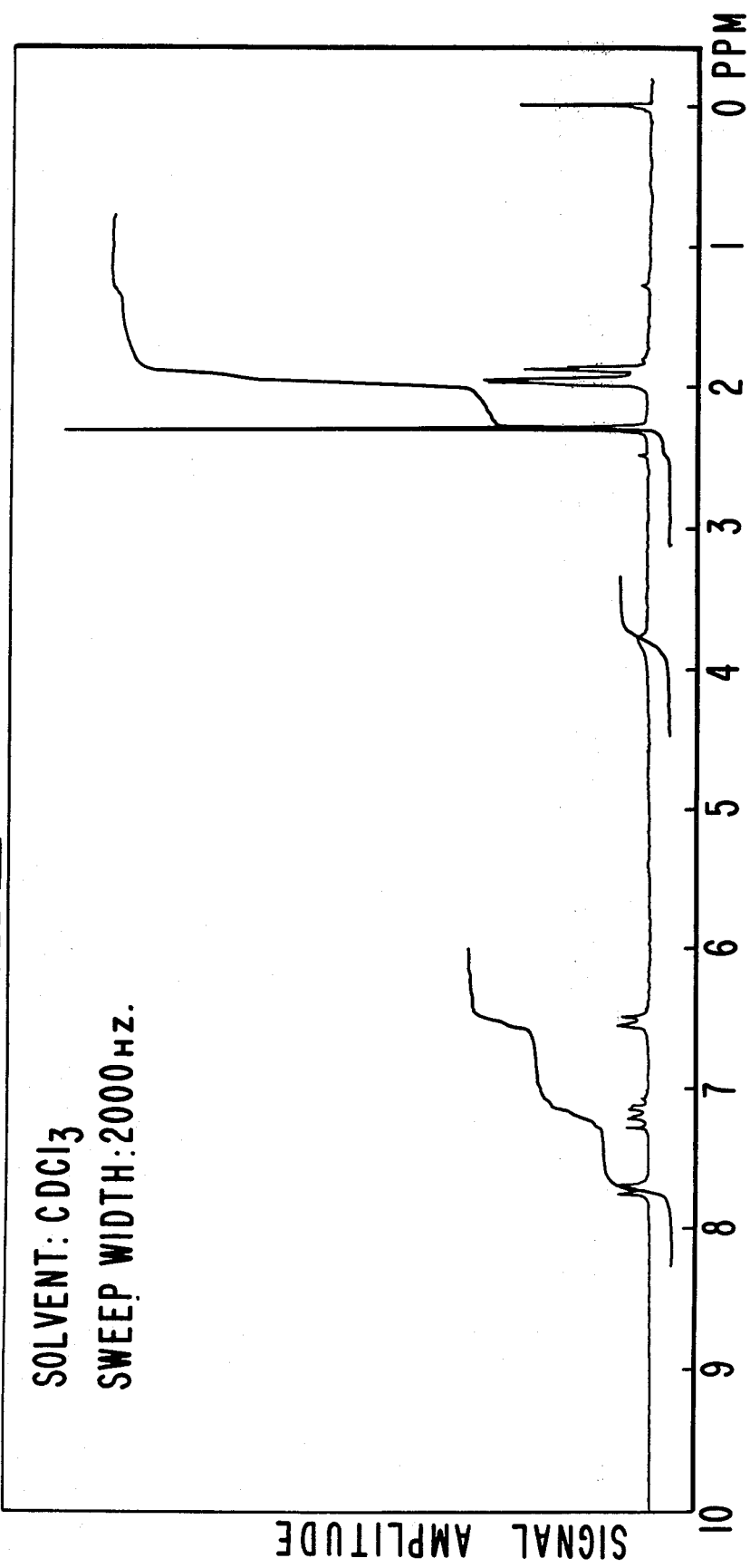

MALTYL-2-METHYL ALKENOATES AND NOVEL PERFUME COMPOSITIONS AND PERFUMED ARTICLES CONTAINING SAME

BACKGROUND OF THE INVENTION

The present invention relates to maltyl-2-methyl alkenoates having the structure:

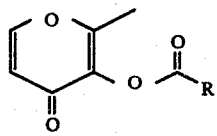

wherein R is an alkenyl moiety having one of the structures:

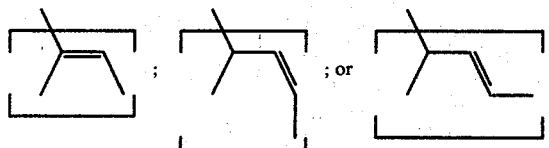

and uses thereof to augment or enhance the aroma of perfume compositions, perfumed articles and colognes.

There has been considerable work performed relating to substances which can be used to augment or enhance or impart aromas to (or in) various consumable materials, such as perfume compositions, perfumed articles and colognes. These substances are used to diminish the use of natural materials, some of which may be in short supply and to provide more uniform properties in the finished product. Sweet, fruity, jammy, pineapple-like, strawberry and green floral aromas and nuances are desirable in perfume compositions, perfumed articles and colognes.

U.S. Pat. No. 4,000,327 issued on Dec. 28, 1976 discloses the use in perfume compositions and perfumed articles of esters of 2-methyl-cis-3-pentenoic acid wherein the ester moiety is lower alkyl having from 2 up to 6 carbon atoms.

British Pat. No. 1,379,038 published on Jan. 2, 1975 includes a broad disclosure of γ,δ-unsaturated carbonyl compounds, useful as flavoring and odoriferous agents of the formula:

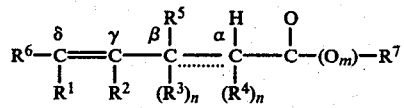

(where m is 0 or 1; n=0 and the dotted line is a bond or n=1 and the dotted line is no bond; $R^1$, $R^2$, $R^3$, $R^4$, $R^5$, $R^6$ and $R^7$ are each H, or linear or branched (a) cyclic, (un)saturated univalent hydrocarbon or oxygen-substituted hydrocarbon; or $R^7$ with $R^3$ or $R^4$ or $R^5$ may form a cycloaliphatic group, provided that $R^3$ and $R^5$ may not contain a multiple bond which is conjugated with the alpha, beta-bond) as being prepared by reacting an alpha-beta-unsaturated carbonyl compound $(R^5)(R^3)_nC=C(C)-(O)_m-R^7$ or halogenated carbonyl compound $X(R^5)(R^3)_n-CH(R^4)_n-C(O)-R^7$ with an organometallic compound comprising a transition metal (preferred: Cu), an univalent cation (preferred: Li+) or [Mg-HALOGEN]+ and an alkenyl radical $R^6-C(R^1)=C(R^2)-$, preferred in the presence of a complexing agent, e.g., diethyl ether, tetrahydrofuran, dimethoxyethane, N-tributylphosphine or trimethylphosphite.

Maltol itself having the structure:

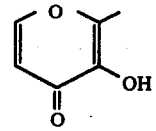

is described by Arctander, "Perfume and Flavor Chemicals (Aroma Chemicals)" at number 1831 as being useful in perfumery.

However, nothing set forth in the above-mentioned prior art or in any other pertinent prior art discloses novel compounds of our invention with structures even remotely similar to the novel compounds of our invention. Furthermore, nothing in the prior art discloses the properties of the compounds of our invention that are unobvious and advantageous in the field of alkenoic acid esters.

BRIEF DESCRIPTION OF THE DRAWINGS

FIG. 7 represents the GLC profile for the reaction product of Example III, which is maltyl tiglate.

FIG. 8 represents the NMR spectrum for the reaction product of Example III, which is maltyl tiglate.

THE INVENTION

Figure 1:
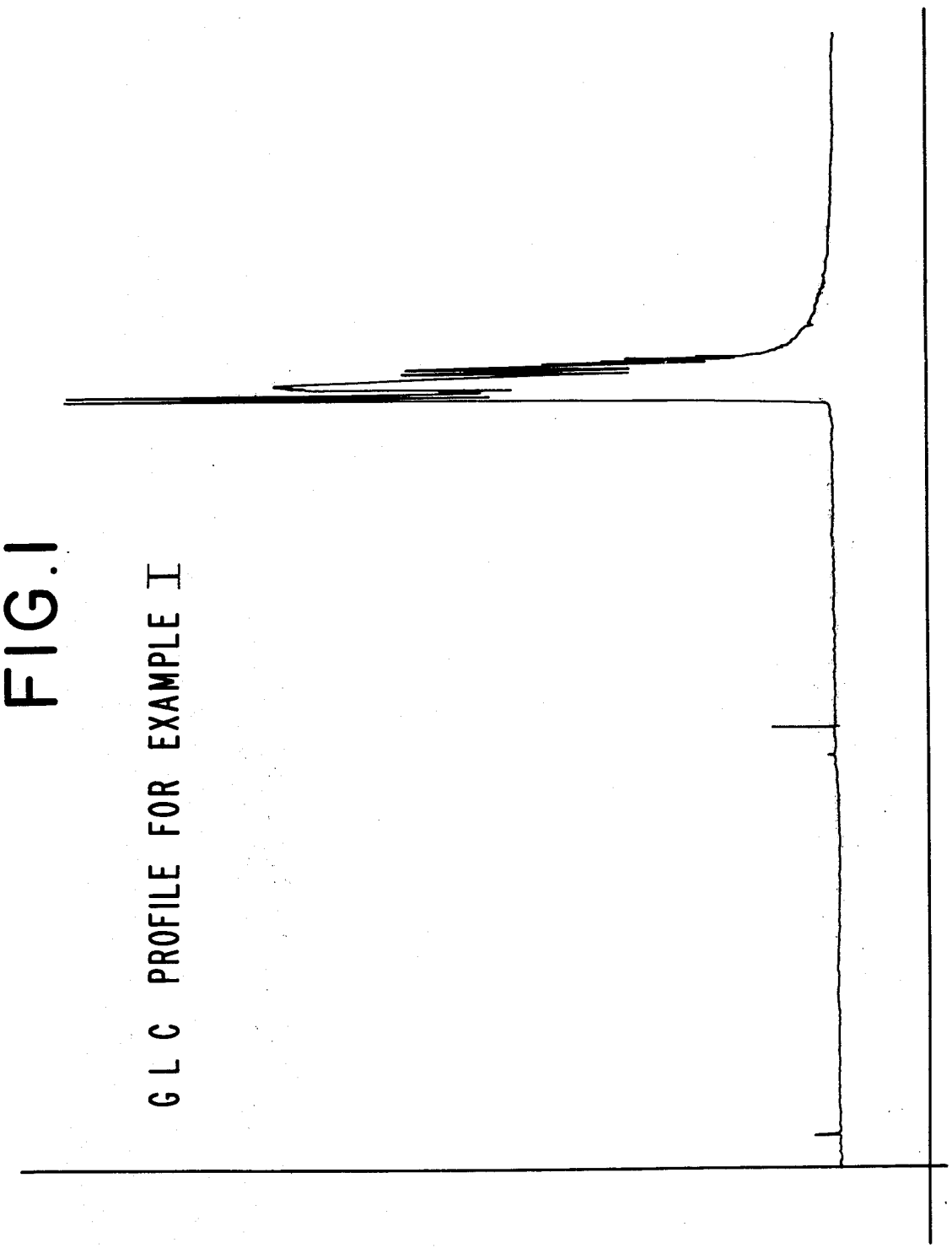
FIG. 1 represents the GLC profile for the reaction product of Example I, which is maltyl-2-methyl-3-pentenoate having a high proportion (greater than 50%) of maltyl-2-methyl-cis-3-pentenoate.

It has now been discovered that solid and liquid perfume compositions, perfumed articles, including soaps, detergents and cosmetic powders and colognes having sweet fresh strawbery/pineapple, sweet, fruity, jammy aromas with green floral nuances may be provided by the utilization of compositions of matter containing one or more maltyl-2-methyl alkenoates having the structure:

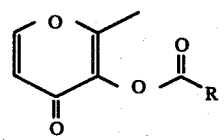

wherein R is one of the moieties:

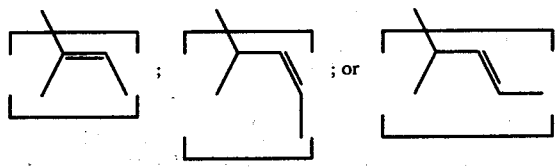

Thus, for example, maltyl-2-methyl-3-pentenoate (having the C.A.S. name 3-hydroxy-2-methyl-4H-pyran-4-one-2-methyl-3-pentenoate) having the structures:

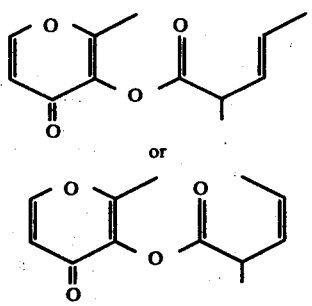

has a sweet fresh strawberry/pineapple aroma with green and floral nuances.

Maltyl tiglate (having the C.A.S. name 3-hydroxy-2-methyl-4H-pyran-4-one tiglate) and the structure:

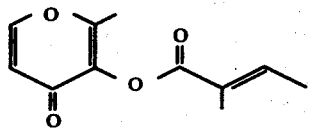

at 1% in food grade ethanol, has a sweet, fruity, jammy, pineapple, strawberry-like aroma.

The maltyl-2-methyl alkenoates of our invention are capable of being formed by first reacting appropriate acid, e.g., tiglic acid or 2-methyl-3-pentenoic acid with a thionyl halide, e.g., thionyl chloride (SOCl₂); then reacting the thus formed acyl halide with maltol thereby producing the maltyl-2-methyl alkenoate which is then subsequently used in perfume compositions, perfumed articles and colognes. The afore-described reaction is illustrated as follows:

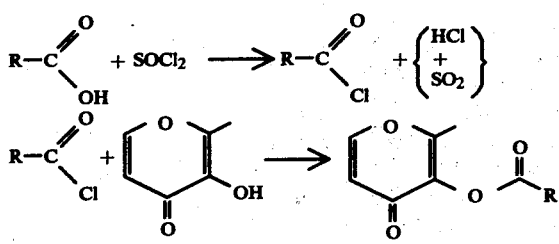

2-Methyl-3-pentenoic acid is produced according to the processes set forth in U.S. Pat. No. 3,984,579 issued on Oct. 5, 1976.

Thus, for example, Example XIV sets forth a method for the preparation of 2-methyl-cis-3-pentenoic acid having a purity of greater than 99%. Example I of U.S. Pat. No. 3,984,579 sets forth a method for producing a cis:trans mixture of 2-methyl-3-pentenoic acid wherein the cis:trans ratio is 60:40. Any of the mixtures of isomers of 2-methyl-3-pentenoic acid produced according to the processes set forth in U.S. Pat. No. 3,984,579 may be used for the purposes of producing the maltyl-2-methyl alkenoates of the instant invention.

One or more maltyl-2-methyl alkenoates and an auxiliary perfume ingredient including, for example, alcohols, aldehydes, nitriles, esters other than the maltyl-2-methyl alkenoates of our invention, cyclic esters (lactones) and natural essential oils may be admixed with the maltyl-2-methyl alkenoates of our invention so that the combined odors of the individual components produce a pleasant and desired fragrance, particularly and preferably in strawberry fragrances. Such perfume compositions usually contain (a) the main note or the bouquet or foundation stone of the composition; (b) modifiers which round off and accompany the main note; (c) fixatives which include odorous substances which lend a particular note to the perfume throughout all stages of evaporation and substances which retard evaporation; and (d) topnotes which are usually low boiling fresh smelling materials.

In perfume compositions, the individual components will contribute its particular olfactory characteristics, but the over-all effect of the perfume composition will be the sum of the effects of each of the ingredients. Thus, one or more of the maltyl-2-methyl alkenoates can be used to alter the aroma characteristic of a perfume composition, for example, by utilizing or moderating the olfactory reaction contributed by another ingredient in the composition.

The amount of maltyl-2-methyl alkenoates of our invention which will be effective in perfume compositions depends on many factors, including the other ingredients, their amounts and the effects which are desired. It has been found that perfume compositions containing as little as 0.3% of maltyl-2-methyl alkenoates or even less (e.g., 0.05%) can be used to impart a scent odor to soaps, cosmetics or other products. The amount employed can range up to 5% of the fragrance components and will depend on considerations of cost, nature of the end product, the effect desired on the finished product and the particular fragrance sought.

The maltyl-2-methyl alkenoates are useful in perfume compositions as an olfactory component in detergents and soaps, space odorants and deodorants, perfumes, colognes, toilet waters, bath preparations, such as bath oils, and bath solids; hair preparations, such as lacquers, brilliantines, pomades and shampoos; cosmetic preparations, such as creams, deodorants, hand lotions and sun screens; powders, such as talcs, dusting powders, face powders and the like. When used as an olfactory component of a perfumed article, as little as 100 parts per million of maltyl-2-methyl alkenoates will suffice to impart a fruity, acrid, strawberry character which is one of the key odor characteristics of strawberry perfume formulations. Generally, no more than 2.0% of one or more maltyl-2-methyl alkenoates based on the ultimate end product is required in the perfume composition.

In addition, the perfume composition or fragrance composition of our invention can contain a vehicle, or carrier for the maltyl-2-methyl alkenoates. The vehicle can be a liquid such as an alcohol, a non-toxic alcohol, a non-toxic glycol, or the like. The carrier can also be an absorbent solid, such as a gum (e.g., gum arabic) or components for encapsulating the composition (such as gelatin).

The following Examples are given to illustrate embodiments of the invention as it is presently preferred to practice it. It will be understood that these Examples are illustrative and the invention is not to be considered restricted thereto except as indicated in the appended claims.

EXAMPLE I

Preparation of Maltyl-2-Methyl-cis-3-Pentenoate Mixture

Reaction:

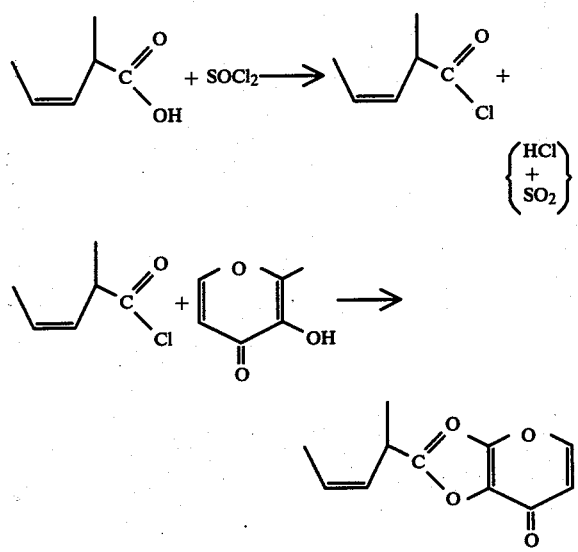

Procedure:

Into a 250 ml two necked reaction flask equipped with mechanical stirrer, Fredrich's condenser and gas trap, 12 g of a mixture containing a high proportion of 2-methyl-cis-3-pentenoic acid prepared according to Example VII at column 18 of U.S Pat. No. 3,984,579 issued on Oct. 5, 1976, in 50 ml benzene is added. Fredrich's condenser side arm is equipped in such a way as to vent the gases released through a trap into a beaker containing commercial preparation of sodium hypochlorite (Clorox ®). With vigorous stirring, 11.9 grams of freshly distilled thionyl chloride are added to the reaction mixture. The reaction mixture is then stirred and heated until no more hydrogen chloride or sulfur dioxide gas is released (over a period of 45 minutes). The reaction mass is then allowed to cool and 12.6 grams of maltol and 50 ml of benzene are added thereto. The mixture is again heated until no more gas evolves (period of time: 45 minutes). The benzene solvent is then removed on a rotary evaporator. The resulting reaction product, maltyl-2-methyl-3-pentenoate containing a high proportion (80%) of maltyl-2-methyl-cis-3-pentenoate and 20% maltyl-2-methyl-trans-3-pentenoate is trapped on a preparative GLC column. Conditions: 12'×⅜" 20% SE-52 column programmed at 100°–190° C. at 8° C. per minute.

A total of 0.55 grams of maltyl-2-methyl-3-pentenoate is collected having a purity of greater than 99%.

Figure 2:
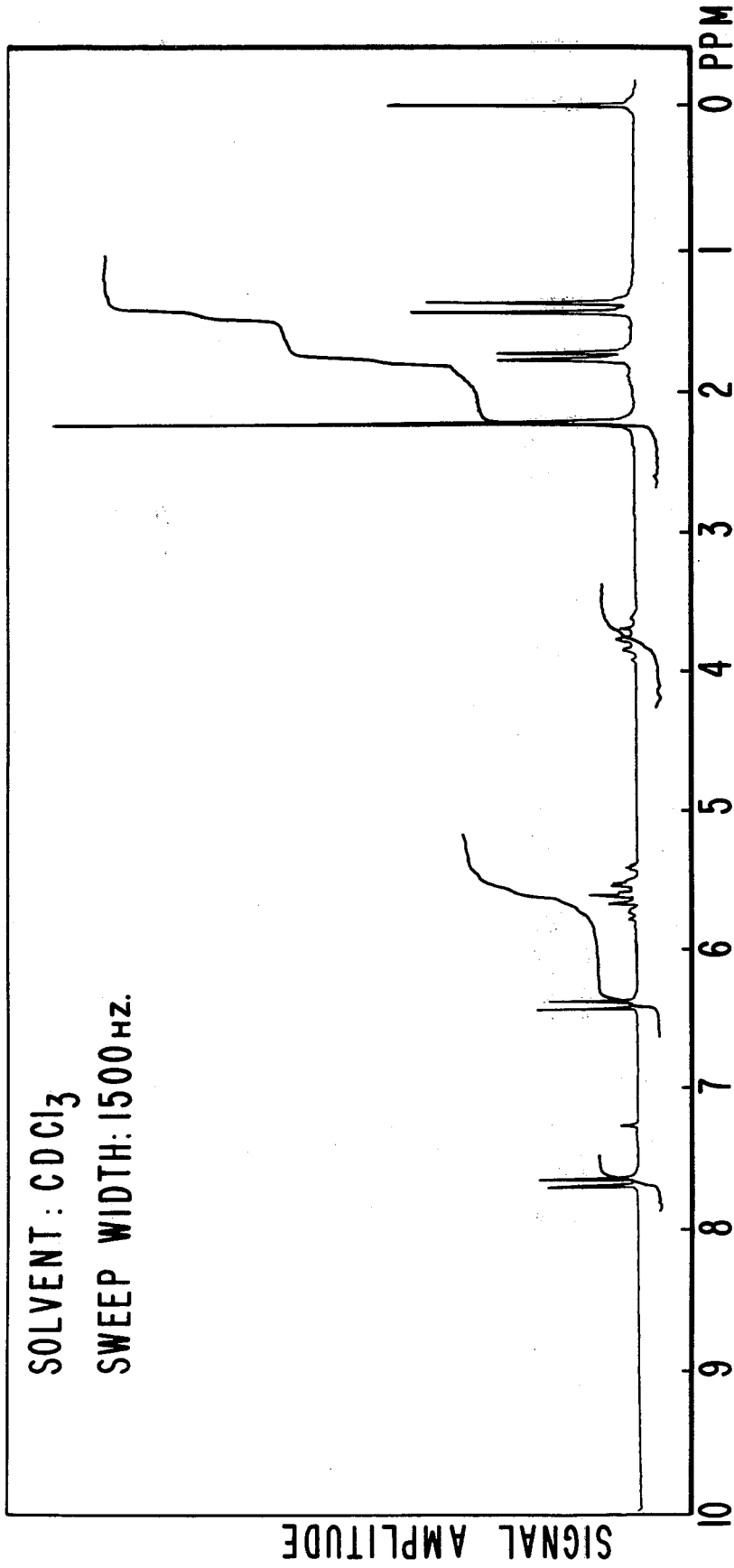
FIG. 2 represents the NMR spectrum for maltyl-2-methyl-3-pentenoate produced according to Example I.
Figure 3:
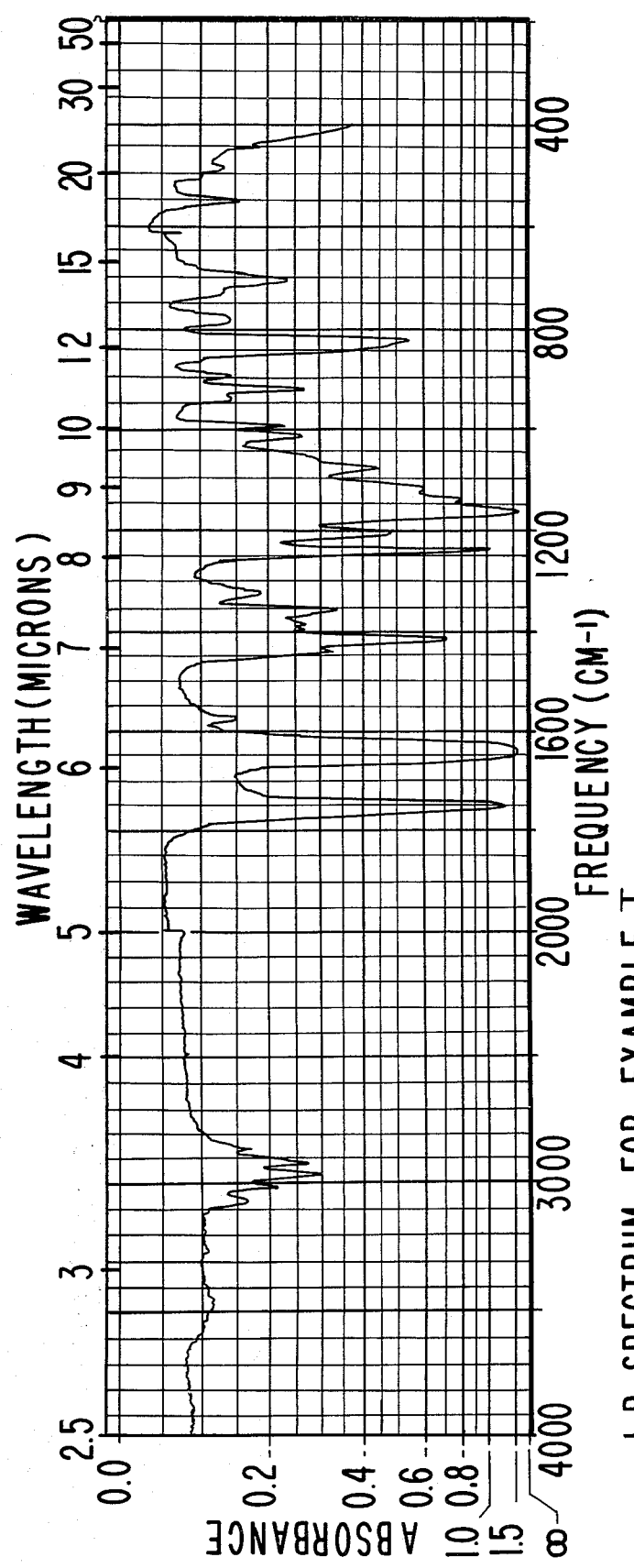
FIG. 3 represents the Infrared spectrum for the reaction product of Example I, which is maltyl-2-methyl-3-pentenoate.

The GLC profile for the reaction product is set forth in FIG. 1. The NMR spectrum is set forth in FIG. 2. The Infrared spectrum for maltyl-2-methyl-3-pentenoate is set forth in FIG. 3.

EXAMPLE II

Preparation of Maltyl-2-Methyl-2-Pentenoate

Reaction:

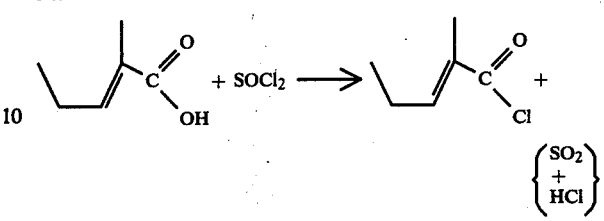

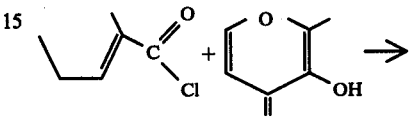

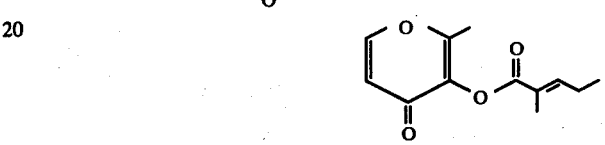

Procedure:

119 Grams of thionyl chloride is distilled immediately before using (75°–76° C. at 760 mm pressure). While the thionyl chloride is being distilled, 114 grams of 2-methyl-2-pentenoic acid (mixture of cis and trans isomers prepared according to the procedure of U.S. Pat. No. 3,499,769 issued on Mar. 10, 1970) is melted using warm water. The melted 2-methyl-2-pentenoic acid and distilled thionyl chloride are then slowly added to a 1 liter three necked round bottomed flask equipped with a mechanical stirrer and a Fredrich's condenser, the side arm of which is equipped with a trap to vent the gas released into a beaker of 5% sodium carbonate. The mixture is stirred and heated for a period of 1 hour. The mixture is then cooled and maltol (126 grams) dissolved in 200 cc of benzene is added. The reaction mass is then heated to reflux and stirred for a period of two hours. After cooling, the reaction mass is filtered to recover a maltol precipitate. The supernatant liquid is then added to a separatory funnel and extracted with three volumes of 5% sodium carbonate. The supernatant liquid is then washed with water. The benzene is then removed using a rotary evaporator and the resulting product is recrystallized from ethyl acetate. The sodium carbonate layer is acidified with 2 molar aqueous hydrochloric acid and extracted with 10% volumes of diethyl ether; then washed with water and dried over anhydrous sodium sulfate; then concentrated to 3.60 grams of residue. This residue is determined to be 2-methyl-2-pentenoic acid.

The recrystallization product from ethyl acetate weighs 30.62 grams and is identified as maltyl-2-methyl-2-pentenoate having a purity of 99.46% (yield: 13.8%).

Figure 4:
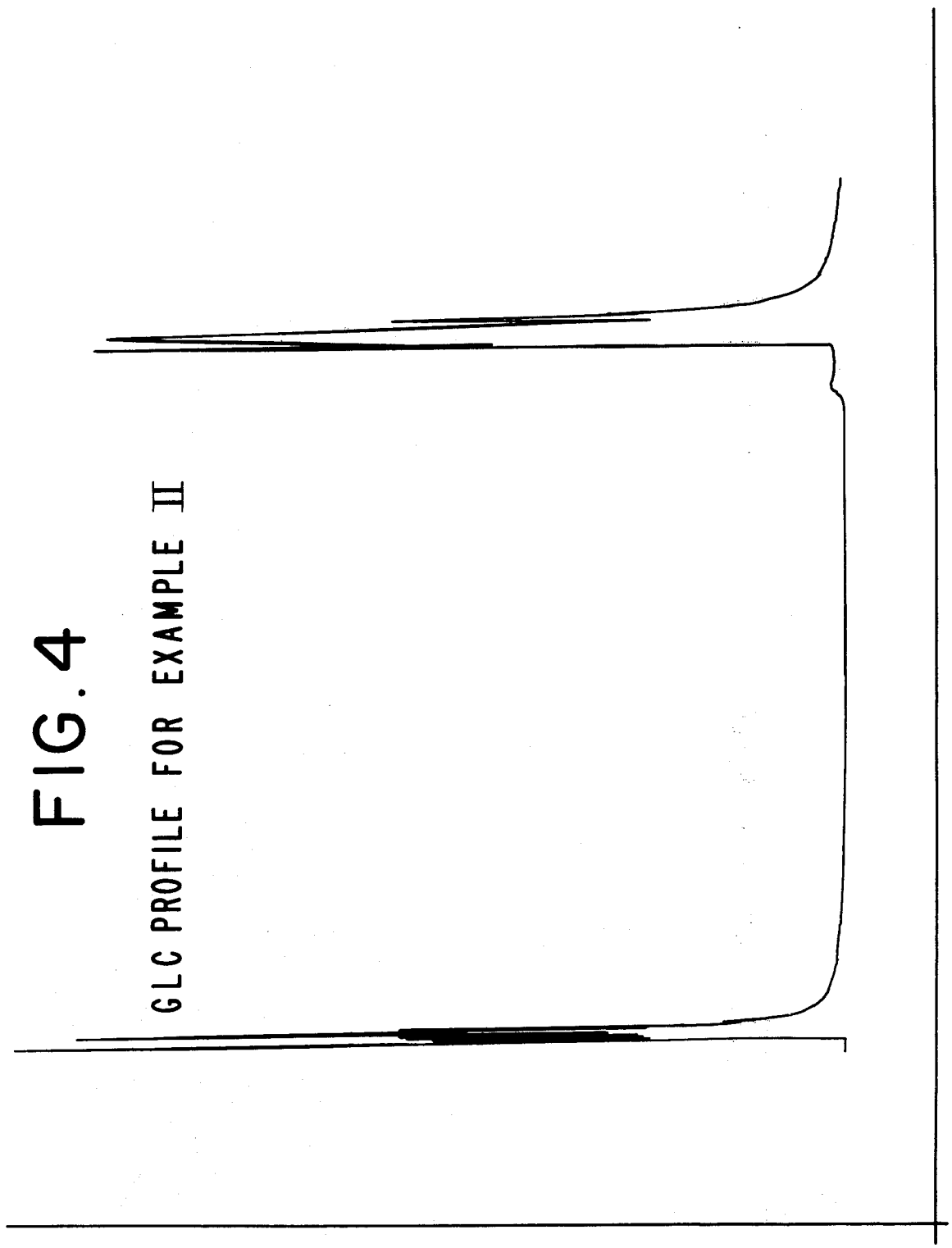
FIG. 4 represents the GLC profile for the reaction product of Example II, which is maltyl-2-methyl-2-pentenoate.
Figure 5:
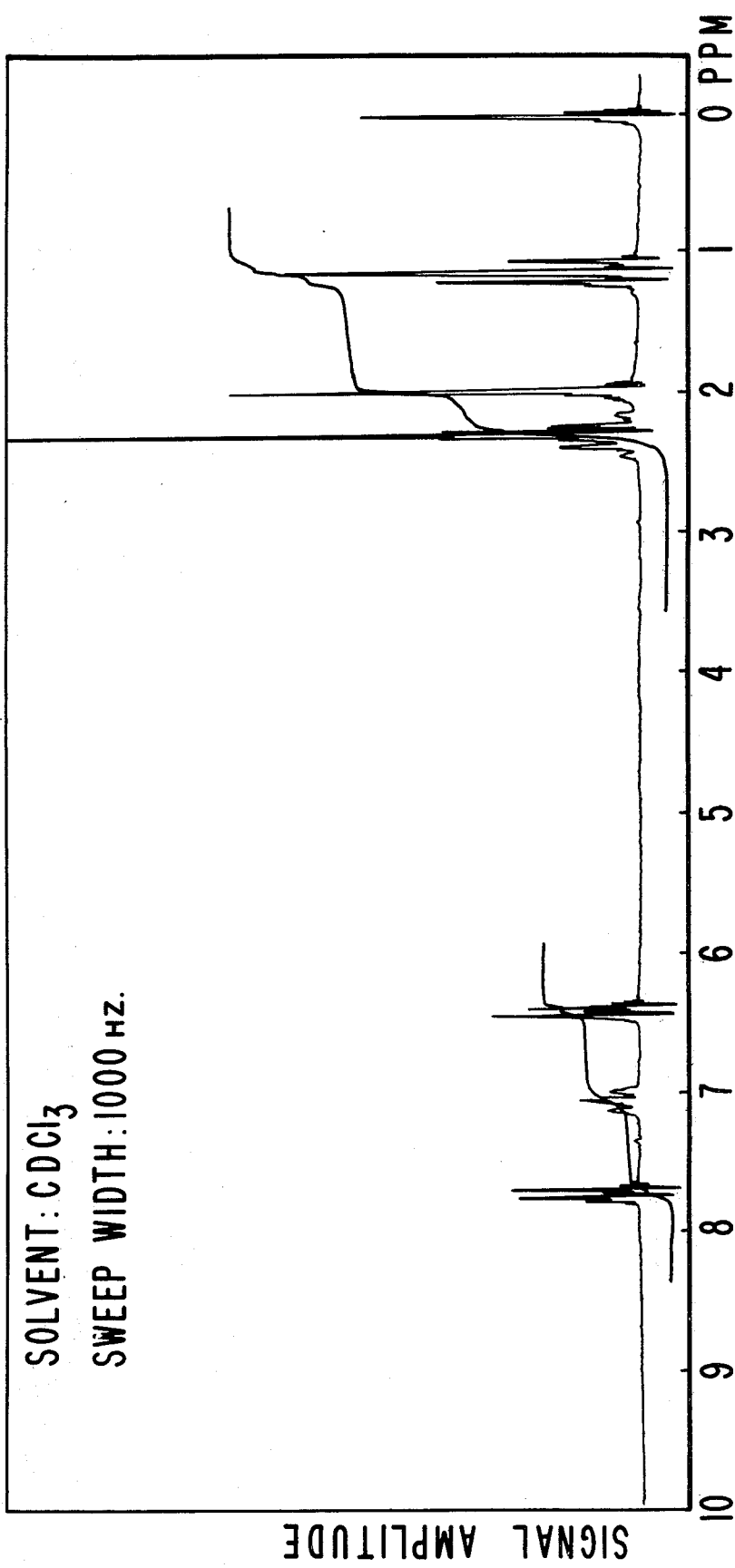
FIG. 5 represents the NMR spectrum for the reaction product of Example II, which is maltyl-2-methyl-2-pentenoate.
Figure 6:
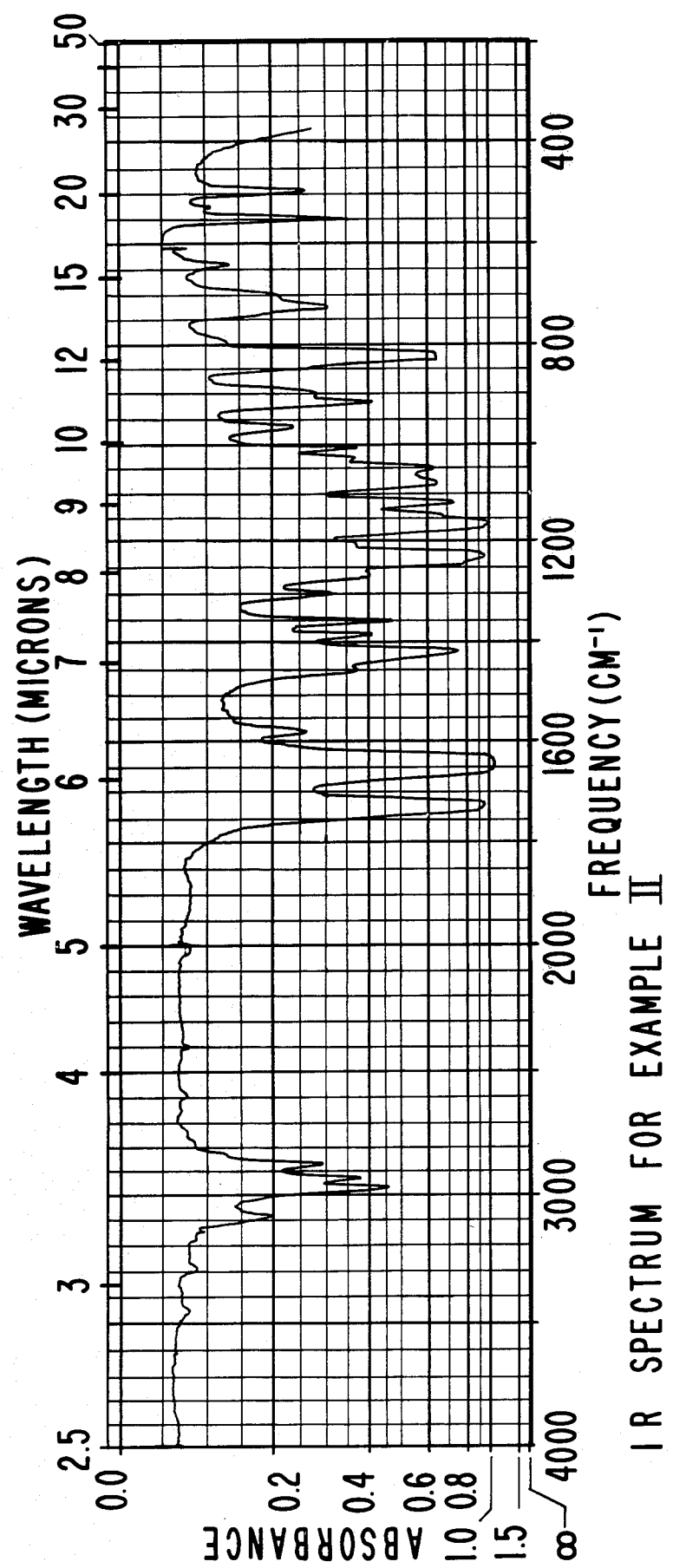
FIG. 6 represents the Infrared spectrum for the reaction product of Example II, which is maltyl-2-methyl-2-pentenoate.

The GLC profile for the reaction product containing maltyl-2-methyl-2-pentenoate is set forth in FIG. 4. The NMR spectrum for maltyl-2-methyl-2-pentenoate is set forth in FIG. 5. The Infrared spectrum for maltyl-2-methyl-2-pentenoate is set forth in FIG. 6.

EXAMPLE III

Preparation of Maltyl Tiglate

Reaction:

7
-continued

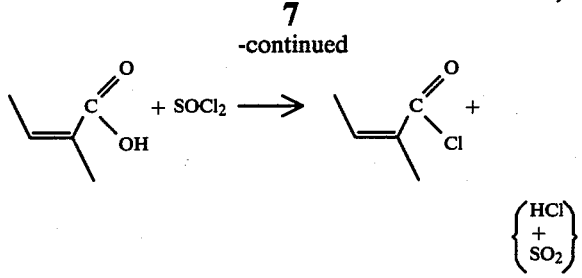

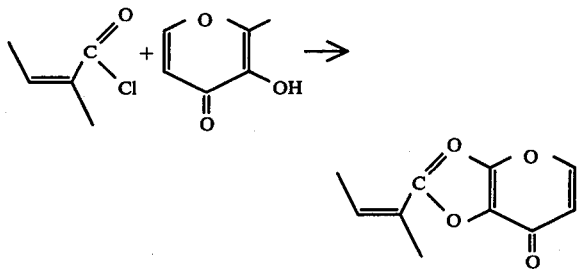

Procedure:

10 Grams of tiglic acid dissolved in 50 ml anhydrous benzene are placed in a 250 ml two necked reaction flask equipped with mechanical stirrer and Fredrich's condenser, whose side arm is equipped in such a way as to vent the gases released during the reaction through a trap and into a beaker containing a solution of sodium hypochlorite (Clorox ®). 11.9 Grams of thionyl chloride (freshly distilled) are added to the reaction mass. The mixture is then stirred and heated until no additional hydrogen chloride or sulfur dioxide is released (period: 60 minutes). The reaction mass is then allowed to cool and 12.6 grams of maltol and 50 cc of benzene are added. The reaction mass is then heated to reflux until no more sulfur dioxide or hydrogen chloride gas is released (period: 1 hour). The benzene is removed on a rotary evaporator.

The reaction mass solidifies upon refrigeration and is then dissolved in ethyl acetate and placed in a freezer. The resultant crystals are filtered and washed with ethyl acetate. The material is then purified by recrystallization from ethyl acetate and a 96.9% pure material is obtained. This material is maltyl tiglate.

The GLC profile for the reaction product is set forth in FIG. 7. The NMR spectrum for maltyl tiglate is set forth in FIG. 8.

EXAMPLE IV

Strawberry Fragrance

The following mixture is prepared:

| Ingredient | Parts by Weight |
| --- | --- |
| Cuminic acetate | 15 |
| Ethyl acetoacetate | 3 |
| Ethyl laurate | 30 |
| Cinnamyl isobutyrate | 15 |
| Cinnamyl decylate | 20 |
| Diacetyl (10% in 95% aqueous ethanol) | 2 |
| Ethyl pelargonate | 5 |
| Gamma undecalactone | 20 |
| Ethyl isobutyrate | 110 |
| Ethyl isovalerate | 60 |
| Ethyl heptanoate | 12 |
| Dulcinyl | 5 |
| 2(para-hydroxyphenyl)-3-butanone | 2 |
| Ethyl acetate | 5 |
| Beta-ionone | 5 |
| Palatone | 3 |
| Vanillin | 10 |

8
-continued

| Ingredient | Parts by Weight |
| --- | --- |
| Ethyl vanillin | 10 |
| Ethyl-3-methyl-3-phenyl glycidate | 70 |
| Maltyl-2-methyl-3-pentenoate prepared according to the process of Example I | 10 |

The mixture containing the maltyl-2-methyl-3-pentenoate prepared according to the process of Example I imparts the berry undertone necessary to complete and round out the strawberry aroma.

EXAMPLE V

Preparation of Maltyl-2-Methyl-cis-3-Pentenoate

Reaction:

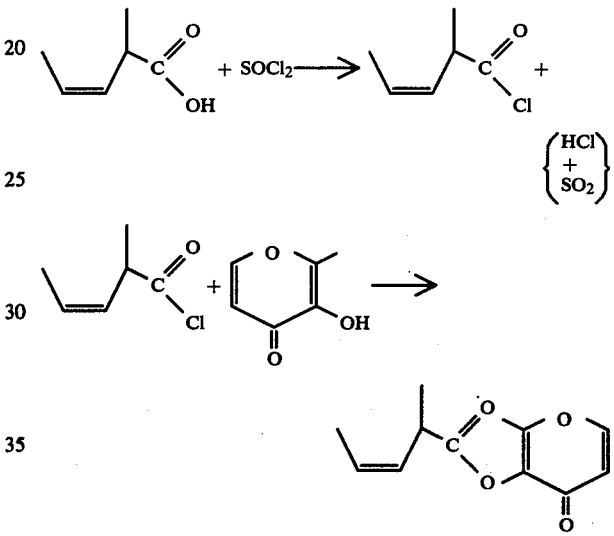

Thionyl chloride is immediately distilled before use (76° at 760 mm pressure) and added to 2-methyl-cis-3-pentenoic acid prepared according to Example XIV at column 30 of U.S. Pat. No. 3,984,579 issued on Oct. 5, 1976. A 1 liter three necked round bottomed flask equipped with a Fredrich's condenser, mechanical stirrer and heating mantle is then used for the reaction. The mixture of 2-methyl-cis-3-pentenoic acid and thionyl chloride is stirred and heated for a period of 1.5 hours (until no more sulfur dioxide or hydrogen chloride gas is emitted). A trap is then connected to the side arm of the Fredrich's condenser and vented into a beaker containing a 5% solution of sodium bicarbonate to trap the evolved hydrogen chloride and sulfur dioxide. The mixture is then allowed to cool to room temperature and 126 grams of maltol in 200 cc of benzene is added. The reaction mass is then heated to reflux for a period of one hour and then cooled. The unreacted 2-methyl-cis-3-pentenoic acid is extracted with 10 equal volumes of 5% sodium carbonate. The resulting reaction product is then washed with water. The resulting mixture is then filtered and the solid is determined to be unreacted maltol (27.44 grams or 44.76%). The benzene is then removed from the supernatant liquid by means of a rotary evaporator, gas chromatography indicating that there remains some 2-methyl-cis-3-pentenoic acid and benzene. The resulting product was purified by means of vacuum distillation whereby the benzene and 2-methyl-cis-3-pentenoic acid are removed. The impurities are distilled off at 4 mm Hg pressure at 70°-80° C. The maltyl-2-cis-3-pentenoate resulting is greater than 99% pure. Yield=114.01 grams or 51.36%.

The sodium carbonate layer is acidified with 2 molar hydrochloric acid and extracted with three 10% volumes of diethyl ether and concentrated to yield 18.9 grams of 34.08% residual 2-methyl-3-pentenoic acid.

GLC, NMR, IR and Mass Spectral data indicate that the material is maltyl-2-methyl-cis-3-pentenoate.

EXAMPLE VI

Strawberry Fragrance

The following mixture is prepared:

| Ingredient | Parts by Weight |
| --- | --- |
| Cuminic acetate | 15 |
| Ethyl acetoacetate | 3 |
| Ethyl laurate | 30 |
| Cinnamyl isobutyrate | 15 |
| Cinnamyl decylate | 20 |
| Diacetyl (10% in 95% aqueous ethanol) | 2 |
| Ethyl pelargonate | 5 |
| Gamma undecalactone | 20 |
| Ethyl isobutyrate | 110 |
| Ethyl isovalerate | 60 |
| Ethyl heptanoate | 12 |
| Dulcinyl | 5 |
| 2(para-hydroxyphenyl)-3-butanone | 2 |
| Ethyl acetate | 5 |
| Beta-ionone | 5 |
| Palatone | 3 |
| Vanillin | 10 |
| Ethyl vanillin | 10 |
| Ethyl-3-methyl-3-phenyl glycidate | 70 |
| Maltyl tiglate prepared according to the process of Example III | 10 |

The mixture containing maltyl tiglate prepared according to the process of Example III imparts a fruity, jammy, pineapple, strawberry undertone to this perfume formulation thereby completing and rounding out the strawberry fragrance thereof.

EXAMPLE VII

Preparation of Soap Composition

One hundred grams of soap chips are mixed with one gram of the perfume composition of Example IV until a substantially homogeneous composition is obtained. The perfumed soap composition manifests an excellent strawberry character with a berry undertone.

EXAMPLE VIII

Preparation of a Detergent Composition

A total of 100 g of a detergent powder is mixed with 0.15 g of the perfume composition of Example IV until a substantially homogeneous composition is obtained. This composition has an excellent strawberry fragrance.

EXAMPLE IX

Preparation of a Cosmetic Powder Composition

A cosmetic powder is prepared by mixing in a ball mill, 100 g of talcum powder with 0.25 g of the maltyl-2-methyl-3-pentenoate produced according to Example V. It has an excellent sweet fresh strawberry/pineapple aroma with green floral nuances.

EXAMPLE X

Perfumed Liquid Detergent

Concentrated liquid detergents with a fruity, strawberry odor are prepared containing 0.10%, 0.15% and 0.20% of maltyl tiglate prepared according to Example III. They are prepared by adding and homogeneously mixing the appropriate quantity of maltyl tiglate in the liquid detergent. The detergents all possess a sweet fruity, jammy, pineapple, strawberry aroma, the intensity increasing with greater concentrations of maltyl tiglate.

EXAMPLE XI

Preparation of a Cologne and Handkerchief Perfume

The composition of Example IV is incorporated in a cologne at a concentration of 2.5% in 85% aqueous ethanol; and into a handkerchief perfume at a concentration of 20% (in 95% aqueous ethanol). The use of the mixture containing maltyl-2-methyl-3-pentenoate in the composition of Example IV affords a distinct and definite strong strawberry aroma with a fruity note to the handkerchief perfume and cologne.

EXAMPLE XII

Preparation of Soap Composition

One hundred grams of soap chips are mixed with 1 gram of maltyl tiglate produced according to Example III until a substantially homogeneous composition is obtained. The perfumed soap composition manifests an excellent sweet fruity, jammy, pineapple, strawberry aroma.

EXAMPLE XIII

Preparation of a Detergent Composition

A total of 100 g of a detergent powder is mixed with 0.15 g of the mixture containing maltyl tiglate produced according to Example III until a substantially homogeneous composition is obtained. This composition has an excellent strawberry aroma with a fruity note.

What is claimed is:

1. Maltyl tiglate having the structure:

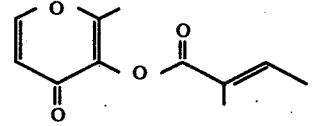

* * * * *